(12) United States Patent
Takahashi et al.

(10) Patent No.: US 7,871,712 B2
(45) Date of Patent: Jan. 18, 2011

(54) DRYING AGENT AND FIELD LIGHT EMISSION DEVICE USING THE SAME

(75) Inventors: Hisamitsu Takahashi, Chiba (JP); Shigeru Hieda, Chiba (JP); Satoshi Tanaka, Chiba (JP)

(73) Assignee: Futaba Corporation (JP)

( * ) Notice: Subject to any disclaimer, the term of this patent is extended or adjusted under 35 U.S.C. 154(b) by 1272 days.

(21) Appl. No.: 11/386,367

(22) Filed: Mar. 22, 2006

(65) Prior Publication Data

US 2006/0216457 A1  Sep. 28, 2006

(30) Foreign Application Priority Data

Mar. 24, 2005 (JP) ............................. 2005-085929
Mar. 16, 2006 (JP) ............................. 2006-071895

(51) Int. Cl.
*H05B 33/04* (2006.01)
*H01L 51/52* (2006.01)
*H01L 51/54* (2006.01)
*C07F 19/00* (2006.01)
*C08G 79/00* (2006.01)

(52) U.S. Cl. ................... 428/690; 428/76; 428/917; 313/504; 313/512; 556/1; 556/175; 556/179; 528/395

(58) Field of Classification Search ................ None
See application file for complete search history.

(56) References Cited

U.S. PATENT DOCUMENTS

| 4,514,555 | A  | * | 4/1985 | Taniguchi et al. ............... 528/9 |
| 6,525,339 | B2 | * | 2/2003 | Motomatsu .................. 257/40 |
| 6,887,592 | B2 | * | 5/2005 | Hieda et al. .................. 428/690 |
| 7,030,258 | B2 | * | 4/2006 | Takahashi et al. ............ 556/175 |
| 2004/0256592 | A1 | * | 12/2004 | Takahashi et al. ............... 252/1 |

FOREIGN PATENT DOCUMENTS

| JP | 9-148066 | 6/1997 |
| JP | 2002-33187 | 1/2002 |
| JP | 2002-231443 | 8/2002 |
| JP | 2003-144830 | 5/2003 |

* cited by examiner

*Primary Examiner*—D. Lawrence Tarazano
*Assistant Examiner*—Andrew K Bohaty
(74) *Attorney, Agent, or Firm*—Quarles & Brady, LLP

(57) ABSTRACT

A water-capturing or drying agent placed in a hermetically sealed field light emission device for maintaining stable light emission of the light emission device not susceptible to moisture and oxygen for long period of time. The drying agent comprises a compound of polymer formed by bonding M constituting a plurality of organometallic compounds wherein M is a trivalent metal atom with an oxygen molecule. The drying agent is placed in the hermetically sealed container, thereby protecting the field light emission device from being adversely affected by damage from trace amounts of moisture permeating from outside the hermetically sealed container and/or adhered to the inner surface thereof.

9 Claims, 5 Drawing Sheets

DRYING AGENT AND FIELD LIGHT EMISSION DEVICE USING THE SAME

CROSS REFERENCES TO RELATED APPLICATIONS

This application claims the priority benefit of Japanese Patent Application No. 2005-085929 filed Mar. 24, 2005 and Japanese Patent Application No. 2006-071895 filed Mar. 16, 2006.

STATEMENT REGARDING FEDERALLY SPONSORED RESEARCH

Not Applicable.

BACKGROUND OF THE INVENTION

The present invention relates to a water-capturing or drying agent capable of absorbing moisture within a sealed container housing electronic components therein for a long period of time. In particular to a thin field light emission device which is capable of mass-producing the thin field emission device with high reliability and is not susceptible to moisture and oxygen for a long period of time and maintains stable emission by using the water-capturing or drying agent.

In general, a field light emission device enclosed in a sealed container comprises a luminescent layer interposed between a pair of electrodes in the hermetically sealed container. There are two types of field light emission devices, one is an organic EL device comprising a luminescent layer composed of mainly fluorescent organic compound, and the other is an inorganic EL device comprising a luminescent layer composed of mainly an inorganic phosphor.

The organic EL device composed of the fluorescent organic compound has a luminescent part which is a laminate formed by interposing an EL layer containing the fluorescent organic compound between an anode and a cathode. Such an organic EL device is a self-luminescent device which injects a hole and an electron into a thin film containing the fluorescent organic compound to re-combine each other to generate an exciton and utilizes emission of fluorescence/phosphorescence at the time of deactivation of the exciton.

The inorganic EL device which is composed of the inorganic phosphor comprises generally a lower electrode, an inorganic phosphor, a dielectric material and an upper electrode which are laminated on the top surface of a substrate in that order and emits light by applying high-frequency voltage between the electrodes.

The organic and inorganic EL devices are hermetically sealed in the container maintaining ultramicromoisture. Since the micromoisture has an adverse effect on characteristics of the EL device, a drying agent is generally placed in the sealed container in order to absorb and/or remove moisture therefrom. The drying agent is frequently referred to as a water-capturing agent, because it captures and absorbs moisture in the EL device housed in the sealed container. Accordingly, the drying agent used in the EL device in the present invention is hereinafter referred to as a water-capturing or drying agent. Embodiments of the water-capturing or drying agent used in the organic EL device will be explained hereinafter.

Since a functional part of the organic EL device is extremely susceptible to damage from moisture, the functional part is hermetically sealed in a container composed of glass or metal so as not to be exposed to the outside. More specifically, the functional part is laminated on a substrate such as glass, over which a sealing cap made of glass or metal is put on the substrate to be bonded to the substrate, thereby confining the functional part in a hermetically sealed container composed of the substrate and the sealing cap. Then, a water-capturing agent such as barium oxide (BaO) or calcium oxide (CaO) is put into the EL device to capture water so that moisture attached to the functional part or being present in an atmosphere inside the hermetically sealed container or permeating into the inside from the hermetically sealed container through a sealing section can be captured as disclosed in Japanese Patent Publication Hei 9-148066.

FIG. 1 is a cross section showing the structure of an example of the organic EL device. The anode 2 made of a transparent conductive film such as ITO (indium tin oxide), the organic layer 3 containing organic EL medium, and the cathode 4 are laminated on the substrate 1 made of glass in that order to form the functional part. Then, the sealing cap 5 formed of metal is put over the EL device to cover the EL device and bonded to the substrate 1 with the adhesive 6 to form the hermetically sealed container. The anode 2 and the cathode 4 penetrate hermetically through the sealing section of the hermetically sealed container to be lead to the outside so as to drive the functional part. A recess 7 is formed at the sealing cap 5, in which powder BaO is filled as the water-capturing or drying agent 8 and sealed with a water permeable film. In this example, the light emitted from the organic layer 3 is passed through the anode 2 and the substrate 1 of glass in the downward direction in FIG. 1.

FIG. 2 is a cross section showing the structure of another example of the organic EL device, in which a recess 10 is formed by countersinking process, such as sandblast, etching, and the like, on one side of the glass plate opposite to the functional part instead of the sealing cap made of metal in FIG. 1. The water-capturing or drying agent 12 made by packing CaO powder with a water-permeable agent or seal-shaped water-capturing agent is adhered to the inner surface of the recess 10 of the sealing substrate 11 made of glass. The rest of the structure is similar to that of shown in FIG. 1. In this example, the light emitted from the organic layer 3 is passed through the anode 2 and the substrate 1 in the downward direction in FIG. 2. It is possible to make the light emitted from the organic layer 3 pass through the cathode 4 and the sealing substrate 11, as disclosed in Japanese Patent Publication 2002-33187 and Japanese Patent Publication 2003-144830, if a light-transmissible cathode and a light-transmissible water-capturing or drying agent. For example, a simple compound of an organometallic compound illustrated by the chemical formula (1) may be used:

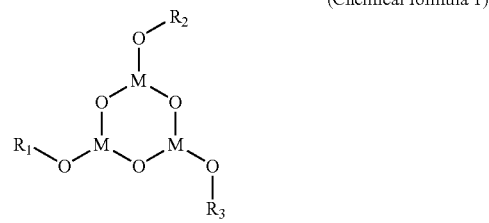

(Chemical formula 1)

In chemical formula (1), $R_1$, $R_2$, and $R_3$ are a hydrogen atom or an alkyl group, aryl group, cycloalkyl group, or heterocyclic ring group having one or more carbon atoms; one or more hydrogen atoms in each of groups may be substituted for a halogen atom; $R_1$, $R_2$, and $R_3$ may be from different groups, may be from the same group, may be bonded to each other, or may be a polymer, and M is a trivalent metal atom.

FIG. 3 is a cross section showing a top emission-type organic EL device using the sealing substrate 13 made of glass in the shape of a plate instead of the sealing substrate 5 made of metal shown in FIG. 1 and the sealing substrate 11 made of glass. The anode 2, the organic layer 3, and the light-transmissible cathode 14 are laminated in that order on the base substrate 1 made of glass. The inorganic water-barrier layer 15 is laminated thereon to form the functional part to which the sealing substrate 13 is bonded via an adhesive layer. Thus, a complete solid sealing structure is formed having no space between the base substrate 1 and the sealing substrate 13. UV-light curable sealing agent 17, for example, epoxy sealing agent is placed onto the periphery of the adhesive layer 16 to seal the adhesive layer 16 between the base substrate 1 and the sealing substrate 13. In this example, the light emitted from the organic layer 3 is passed through the cathode 14, the adhesive layer 16, and the sealing substrate 13 in the upward direction in FIG. 3 as disclosed in Japanese Patent Publication 2002-231443.

In the organic EL device shown in FIG. 1, the recess 7 is formed on the sealing cap 5 for sealing the functional part on the base substrate 1 by a press molding process. In the organic EL device shown in FIG. 2, the recess 10 is formed on the sealing substrate 11 by a countersinking process. The recess 7 or 10 is filled with BaO or CaO powder as a drying agent for capturing water in the organic EL device. A water-capturing or drying agent in the shape of a sheet formed of the BaO or CaO powder may be applied to the recess 7 or 10. However, if the recess 7 or 10 is filled with a required amount of the water-capturing agent powder, the thickness thereof becomes 0.2 mm at the minimum, and the recess 7 or 10 must have at least 0.3 to 0.5 mm in thickness. As a result, the thickness of the sealing substrate 11 or the sealing cap 5 becomes large, and the thickness of the organic EL device as a whole becomes thick.

BaO and CaO used for a water-capturing or drying agent in the EL device are liable to scatter, because BaO and CaO are powder. Thus, it is necessary to inhibit the scattering thereof when sealing them into the recess 7 or 10. This creates such a problem that workability is bad, automation is difficult, and the adhesion strength of the seal lowers if the BaO or CaO powder is adhered to the area to be coated.

In the organic EL device shown in FIG. 3, TFT circuit is formed on the surface of the base substrate 1 on the side of the anode 2, on which the functional part is laminated. Consequently, the light emitted from the organic layer 3 of the functional part can not pass through the anode, but instead passes through the cathode 14 via the sealing substrate 13 as described above. The BaO or CaO powder as a water-capturing agent or a water-capturing agent in the shape of sheet using the BaO or CaO powder is not transparent. Thus, the water-capturing or drying agent can not be placed on the cathode 14 through which light passes in the organic EL device shown in FIG. 3.

On the other hand, improved water-capturing performance can be expected when a solution of the single compound of the light transmissible organometallic compound, for example, shown in chemical formula (1) of Japanese Patent Publication 2002-33187 dissolved in an organic solvent, is applied as a water-capturing or drying agent on the inner surface of the recess 10 formed in the sealing substrate 11 by countersinking.

Inventors of the present invention have reviewed the molecular structure of a single compound of the conventional water-capturing or drying agent shown in the chemical formula (1) in order to improve the water-capturing effect. Inventors of the present invention have inferred that the water-capturing effect can be improved by bonding the water-capturing or drying agent shown in the chemical formula (1) with an oxygen molecule to make the reaction with water easy to occur.

The present invention improves the reliability of the EL device by using as a water-capturing or drying agent an organometallic compound illustrated by the chemical formula (5):

(Chemical formula 5)

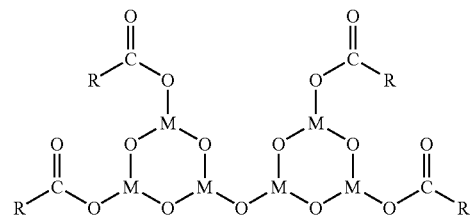

wherein M is a trivalent metal atom.

By dimerizing the organometallic compound illustrated by the chemical formula (1) as shown in the formula (5) to form a molecular structure of dimer, torsion is generated in the molecule and the molecule of water becomes easy to attack an oxygen atom at the crosslinking section of the dimer. On the other hand, the water-capturing or drying agent of the prior art shown in chemical formula (1) has a hydrophobic substituent in the single compound. Thus, a water molecule is hard to approach it. Accordingly, the reaction of the conventional water-caturing or drying agent with water is hard to occur, thereby decreasing the water-capturing or drying performance.

A reaction formula with water is shown in reaction formula (6):

(Reaction formula 6)

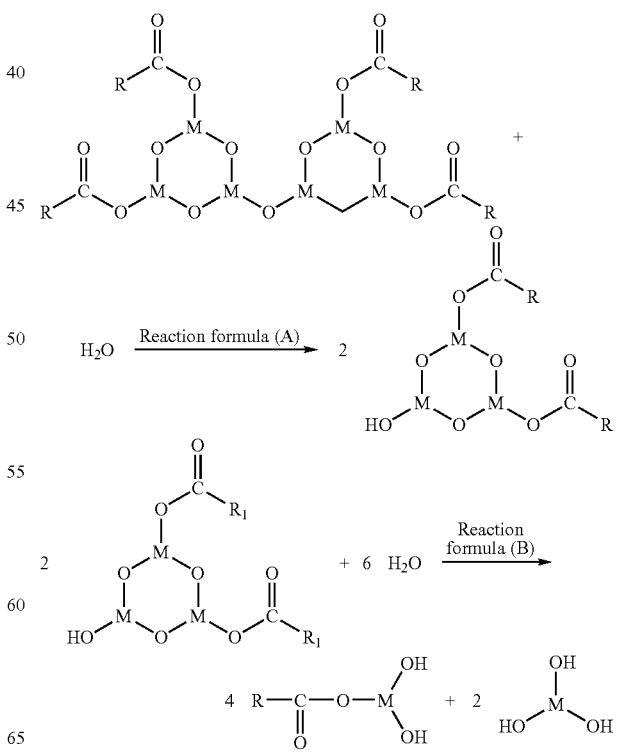

The dimer compound illustrated by the chemical formula (5) reacts with water to form a monomer of six-membered ring shown in the chemical formula (1) as shown in the reaction formula (A) of the above chemical formula (6). As a result, the compound in the chemical formula (5) absorbs water and acts as a water-capturing or drying agent. In the chemical formula, M is a trivalent metal atom. Then, the monomer of six-membered ring reacts with water as shown in the reaction formula (B) of the above chemical formula (6). After such reaction proceeds completely, hydroxide of trivalent metal M (OH)$_3$ is generated. As a result, the compound absorbs water and acts as a water-capturing or drying agent. Similarly, the reaction with trimer, tetramer and pentamer, as well as a polymer of the organometallic compound shown by chemical formula (1) proceeds and water-capturing or drying effect increases.

An example of the trimer is shown in chemical formula (7).

(Chemical formula 7)

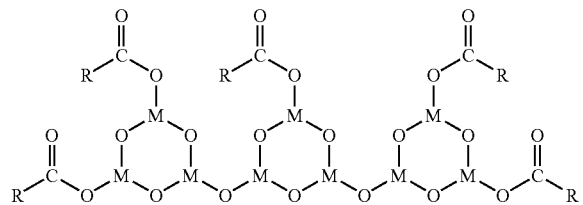

wherein M is a trivalent metal atom.

An example of the tetramer is shown in chemical formula (8).

By dimerizing, trimerizing, tetramerizing, pentamerizing or polymerizing the molecular structure in such a manner as described above, torsion is generated in a molecule and the molecule of water becomes easy to attack an oxygen atom at crosslinked section. On the other hand, the water-capturing or drying agent of prior art shown in chemical formula (1) has a hydrophobic substituent. Thus, a water molecule is hard to approach. Accordingly, the reaction of the conventional water-capturing or drying agent with water is hard to occur, and water-capturing performance is decreased.

In addition to the compounds shown by the above chemical formulae (2) to (4), various kinds of polymers obtained by bonding a plurality of organometallic compounds having a trivalent metal atom M with an oxygen atom have torsion in their molecules. A water molecule is, therefore, easy to attack an oxygen atom at a crosslinked section to impart the water-absorbing effect to such various kinds of polymers. The metal atom M may be Al, Ga, In, La, Y and other trivalent metal atom.

Examples of compounds illustrated by chemical formula (1) in which $R_1$, $R_2$ and $R_3$ are substituted are those illustrated by the following chemical formulae (10), (11) and (12).

(Chemical formula 8)

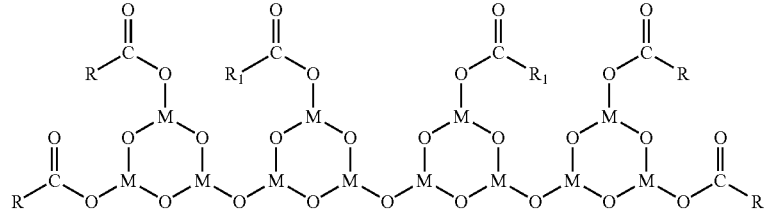

wherein M is a trivalent metal atom.

Another example of the tetramer is shown in chemical formula (9).

(Chemical formula 9)

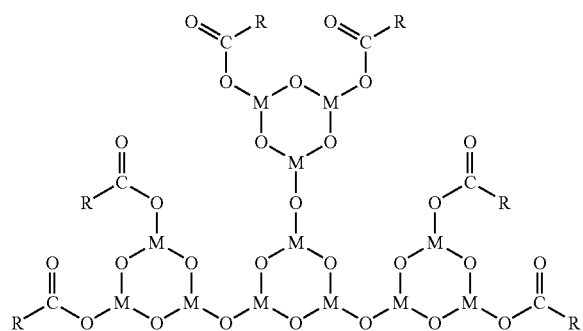

wherein M is a trivalent metal atom.

(Chemical formula 10)

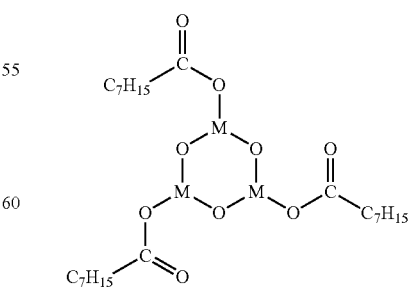

wherein M is a trivalent metal atom.

(Chemical formula 11)

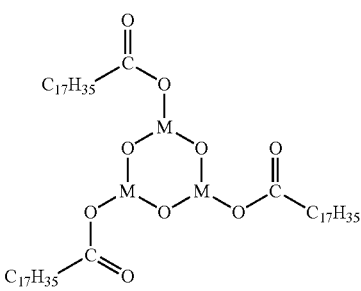

wherein M is a trivalent metal atom.

(Chemical formula 12)

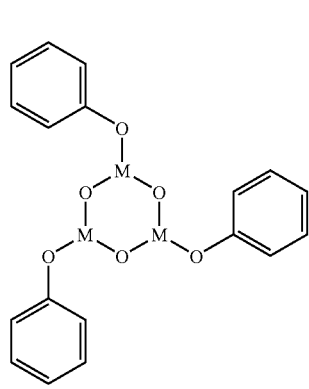

wherein M is a trivalent metal atom.

In the formulae, R is one selected from the group consisting of an alkyl group, aryl group, cycloalkyl group, heterocyclic group. Alkyl group may be exemplified by a methyl group, ethyl group, propyl group, butyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, heneicosyl group, docosyl group, and the like.

Aryl group may be exemplified by a phenyl group, tolyl group, 4-cyanophenyl group, biphenyl group, o,m,p-terphenyl group, naphthyl group, anthranyl group, phenanthrenyl group, fluorenyl group, 9-phenylanthranyl group, 9,10-diphenylanthranyl group, pyrenyl group, and the like.

Cycloalkyl group may be a cyclopentyl group, cyclohexyl group, norbornane group, adamantane group, 4-methylcyclohexyl group, 4-cyanocyclohexyl group and the like.

Examples of heterocyclic group may be a pyrrole group, pyrroline group, pyrazole group, pyrazoline group, imidazole group, triazole group, pyridine group, pyridazine group, pyrimidine group, pyrazine group, triazine group, indole group, benzimidazole group, purine group, quinoline group, isoquinoline group, cinorin group, quinoxaline group, benzquinoline group, fluorenone group, dicyanofluorenone group, carbazole group, oxazole group, oxadiazole group, thiazole group, thiadiazole group, benzoxazole group, benzothiazole group, benzotriazole group, bisbenzooxazole group, bisbenzothiazole group, bisbenzoimidazole group and the like.

SUMMARY OF THE INVENTION

The present invention provides a water-capturing or drying agent placed in a hermetically sealed container having electronic components therein for absorbing moisture within the container for a long period of time.

According to the present invention, there is provided a water-capturing or drying agent including at least a polymer formed by bonding a metallic atom of an organometallic compound having a multiple-membered ring structure with an oxygen molecule. More particularly, the present invention is directed to a water-capturing or drying agent including at least a polymer formed by bonding a plurality of compounds illustrated by chemical formula (1) with an oxygen atom. In chemical formula (1):

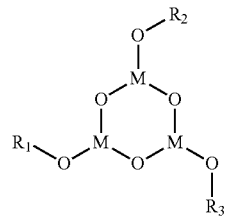

$R_1$, $R_2$, and $R_3$ are a hydrogen atom or an alkyl group, aryl group, cycloalkyl group, or heterocyclic ring group having one or more carbon atoms; one or more hydrogen atoms in each of groups may be substituted for a halogen atom; $R_1$, $R_2$, and $R_3$ may be from different groups, may be from the same group, may be bonded to each other, or may be a polymer, and M is a trivalent metal atom.

According to another aspect of the present invention, there is provided a water-capturing or drying agent comprising a compound illustrated by chemical formula (2). In chemical formula (2):

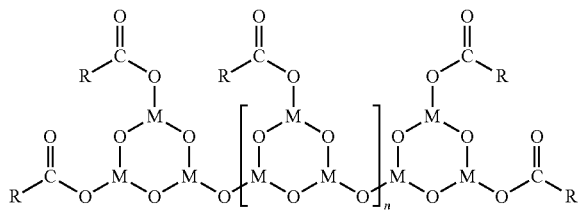

R is a hydrogen atom or an alkyl group, aryl group, cycloalkyl group, heterocyclic ring group having one or more carbon atoms; one or more hydrogen atoms in each of groups may be substituted for a halogen atom; R maybe from different groups, may be from the same group, may be bonded to each other, or may be a polymer; n is 0 or an integer of 1 and above; and M is a trivalent metal atom.

According to still another aspect of the present invention, there is provided a water-capturing or drying agent including a compound illustrated by chemical formula (3). In chemical formula (3):

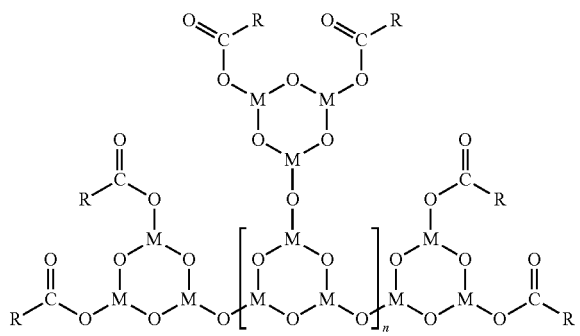

R is a hydrogen atom or an alkyl group, aryl group, cycloalkyl group, heterocyclic ring group having one or more carbon atoms; one or more hydrogen atoms in each of groups may be substituted for a halogen atom; R may be from different groups, may be from the same group, may be bonded to each other, or may be a polymer n is 0 or an integer of 1 and above; and M is a trivalent metal atom.

According to an additional aspect of the present invention, there is provided a water-capturing or drying agent including a compound illustrated by chemical formula (4). In chemical formula (4):

hermetically sealed container is provided. In the field light emission device, a compound of polymer formed by bonding a metallic atom of an organometallic compound having a multiple-membered ring structure with an oxygen molecule is placed in the container. The organometallic compound having a multiple-membered ring structure placed in the container acting as a water-capturing or drying agent is one of compounds illustrated by the chemical formulae (2), (3) and (4) which is formed of a plurality of organometallic compounds having a multiple-membered ring structure illustrated by the chemical formula (1) bonded by at least one metallic atom. According to an embodiment of the present invention, the organometallic compound illustrated by the chemical formulae (2), (3) and (4) is placed in the hermetically sealed container together with an ultraviolet light-curing agent. This facilitates placing the water-capturing or drying agent in the container. The ultraviolet light-curing agent is preferably a light-transmissible monomer having a lipophilic group which makes it possible to place the water-capturing or drying agent in the container easily and to provide the transparent water-capturing or drying agent with the field light emission device.

BRIEF DESCRIPTION OF THE DRAWINGS

These and other objects, features, and advantages of the present invention will become more apparent upon a reading of the following detailed description and drawings, in which:

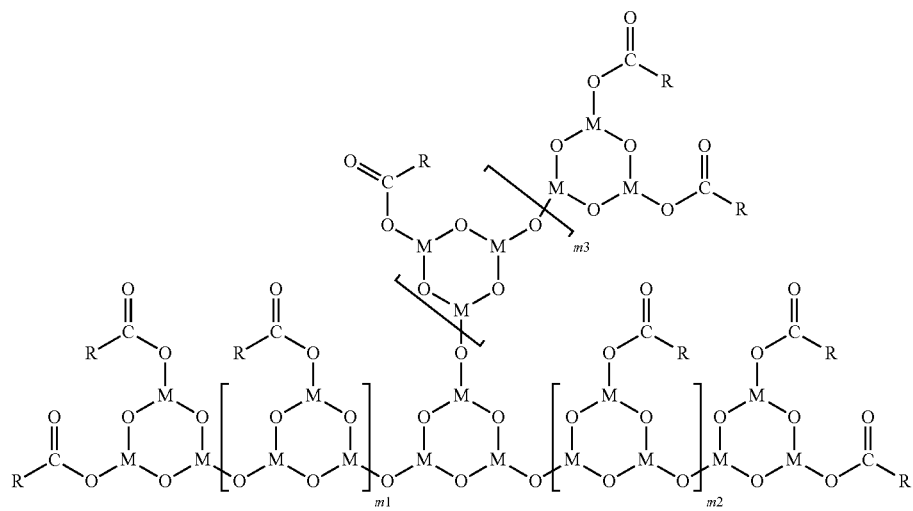

R is a hydrogen atom or an alkyl group, aryl group, cycloalkyl group, heterocyclic ring group having one or more carbon atoms; one or more hydrogen atoms in each of groups may be substituted for a halogen atom; R may be from different groups, may be from the same group, may be bonded to each other, or may be a polymer; $m_1$, $m_2$ and $m_3$ are an integer of 1 and above and may be different each other or the same as each other; and M is a trivalent metal atom.

Figure 1:
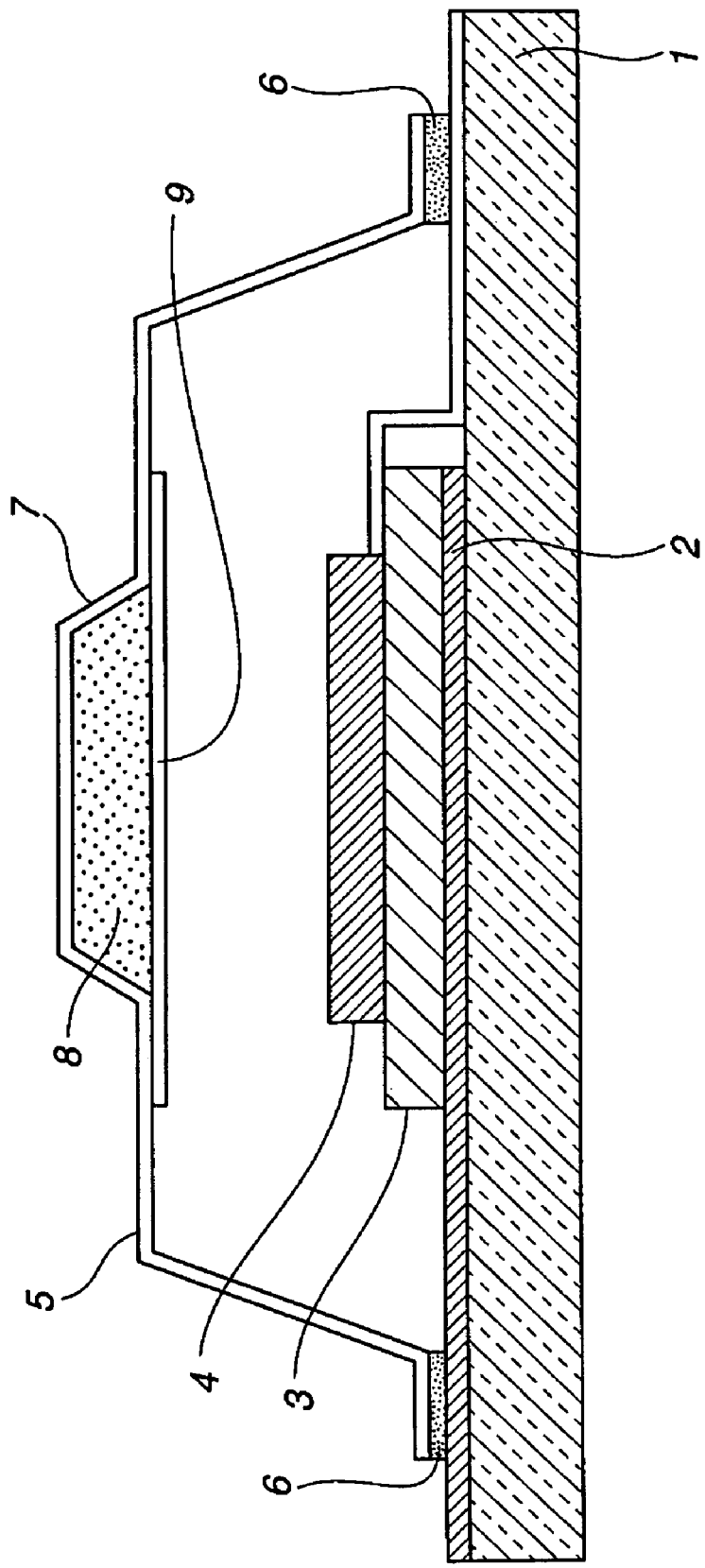
Figure 2:
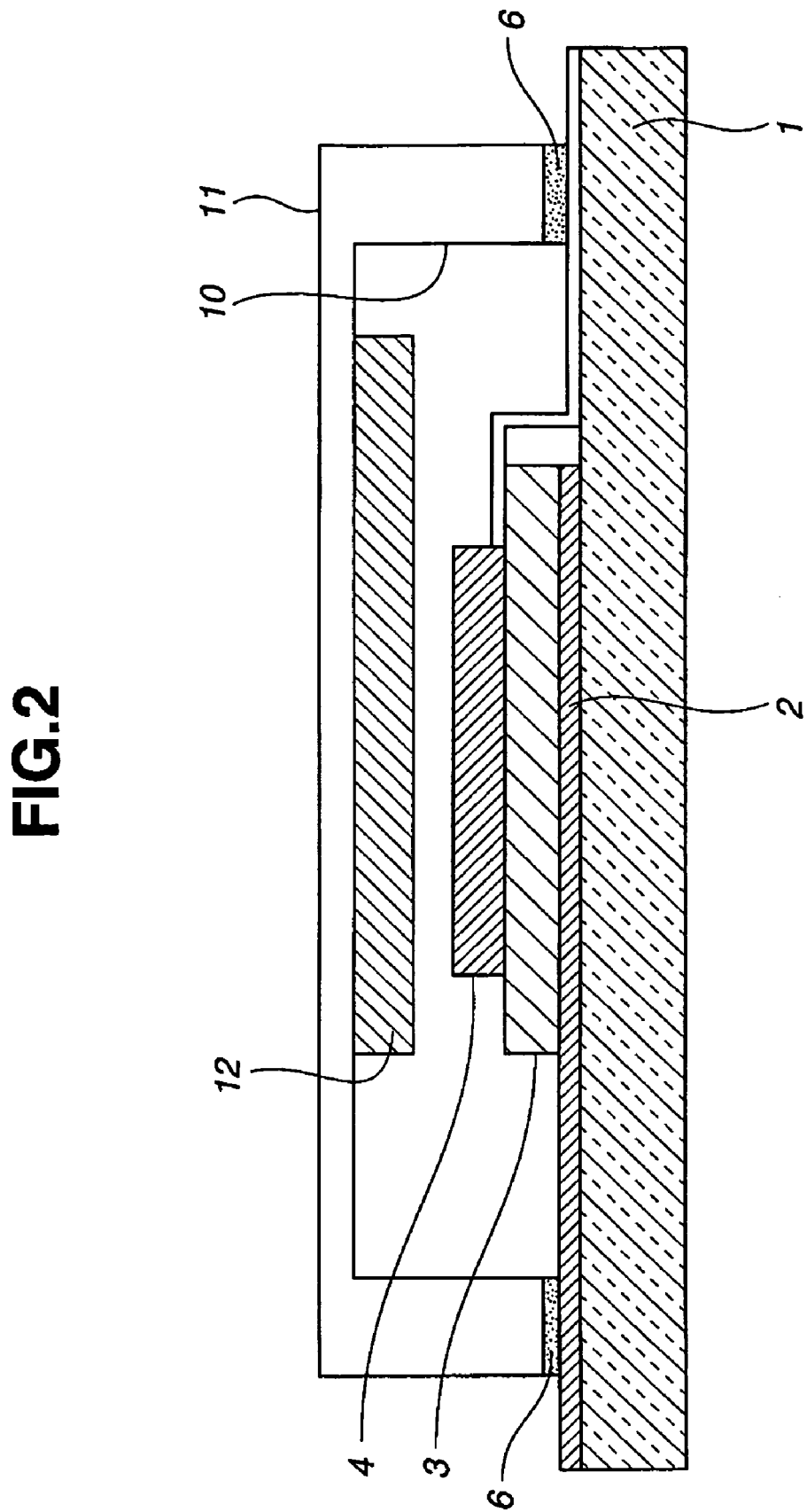
Figure 3:
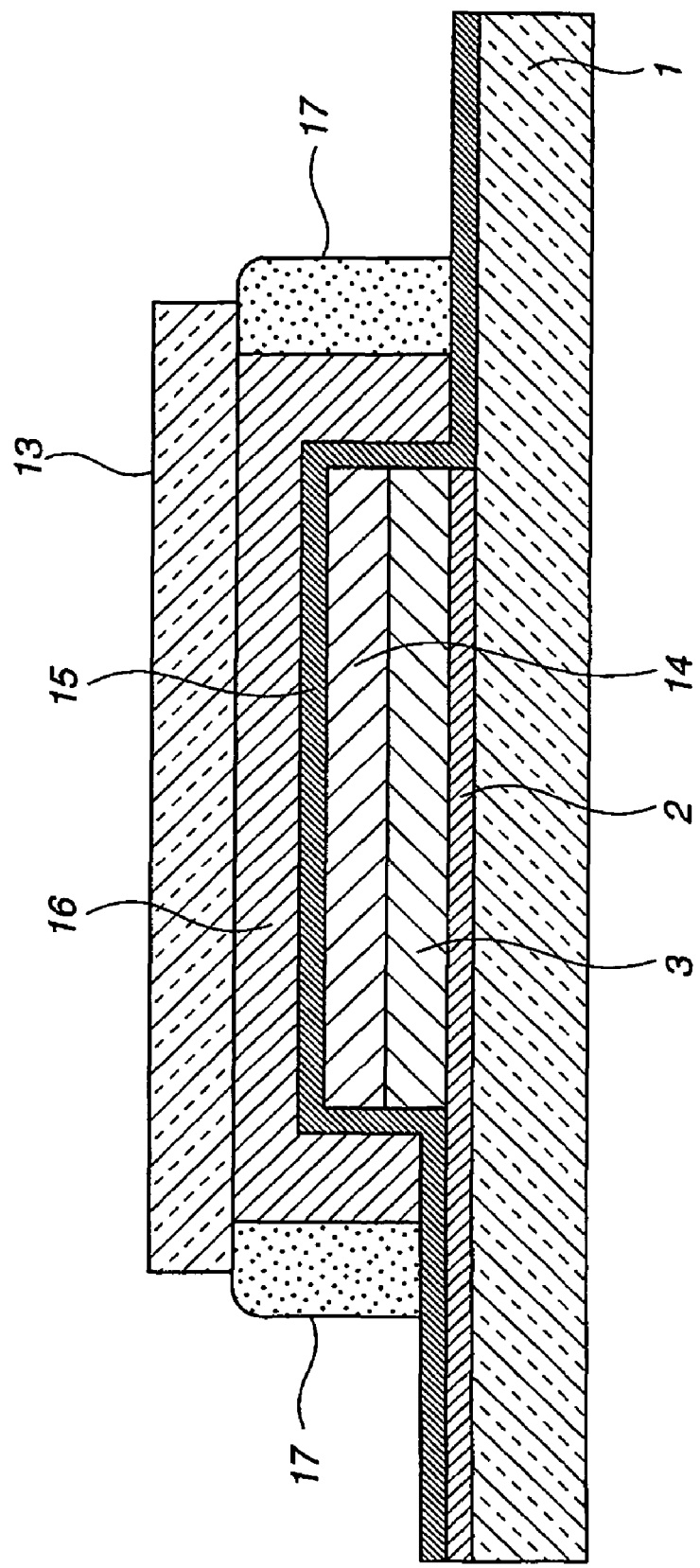
Figure 4:
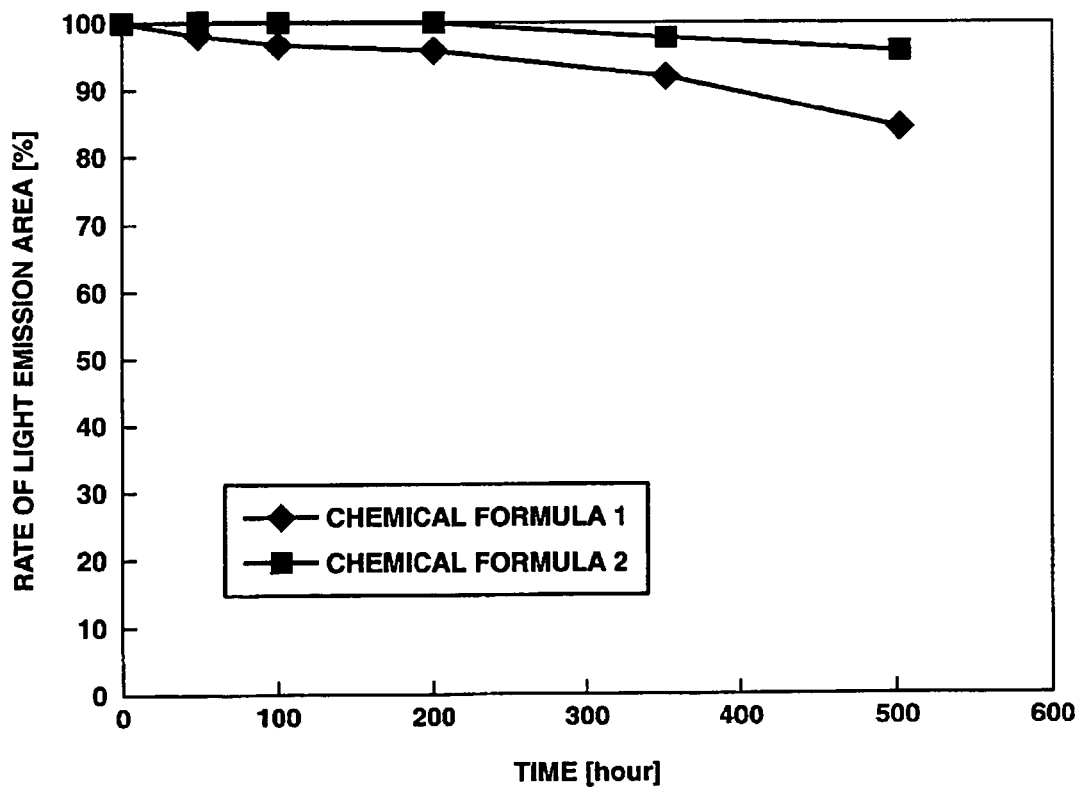
Figure 5:
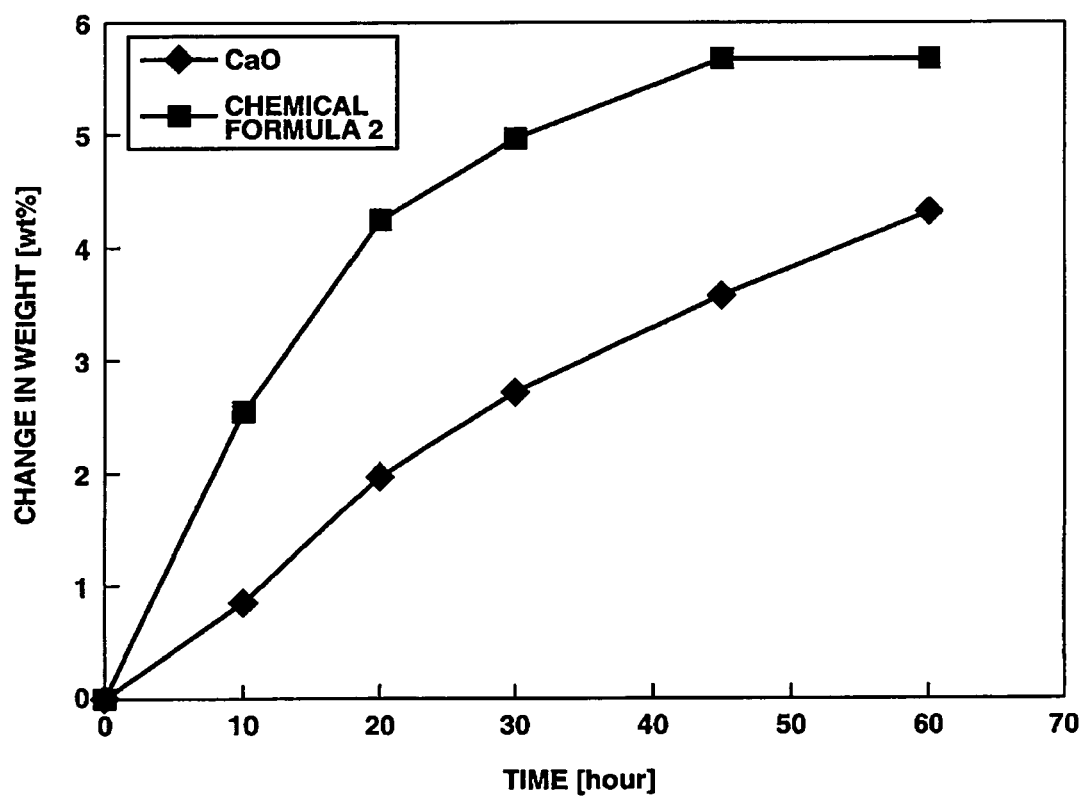

According to an alternative form of the present invention, a field light emission device having a light emission layer in a FIG. 1 is a cross section showing an example of the structure of an organic EL device;

FIG. 2 is a cross section showing another example of the structure of an organic EL device;

FIG. 3 is a cross section showing a further example of the structure of an organic EL device;

FIG. 4 is a graph showing the change in the rate of light emission area of the water-capturing agent shown in the chemical formulae (1) and (2); and FIG. 5 is a graph showing the change in weight of CaO and the water-capturing agent shown in the chemical formula (1).

DETAILED DESCRIPTION OF THE PREFERRED EMBODIMENTS

The present inventors have developed an organometallic compound having a trivalent atom and two or more of six-membered ring structures as a novel water-capturing or drying agent. This novel water-capturing agent has a water-capturing effect and performance comparable or superior to the conventional water-capturing or drying agent. By using the novel water-capturing or drying agent of the present invention, the growth of a darkspot can be suppressed, and shelf life and useful service life of the organic EL device can be significantly improved. Further, the film forming properties of the water-capturing or drying agent of the present invention are good and a uniform film can be formed on a countersunk glass by means of a dispenser application. The water-capturing or drying agent can also be applied using a spinner, a spray-inkjet method, a doctor blade method, a screen printing method, an offset printing method, and the like, without departing from the scope of the invention. Since the novel water-capturing or drying agent of the present invention can be formed into a uniform and transparent thin film, emission of EL device can be viewed through the transparent film. Further, a water-capturing or drying agent effective for a top-emission type organic EL device can be provided. In addition, the water-capturing or drying agent of the present invention can react with moisture and absorb trace quantity of moisture in the device faster than a conventional powder-type water-capturing or drying agent, the growth of a darkspot can be suppressed, and the water-capturing or drying agent for the field light emission device or electronic components enclosed in a hermetically sealed container can be provided.

The present invention will be more clearly understood with reference to the following examples.

Example 1

Water-Capturing or Drying Agent Containing Aluminum (Al) as a Trivalent Metal Constituting an Organometallic Compound Having a Multi-Membered Ring Structure (Method of synthesis) 6.13 g of aluminum triisopropoxide (AIP), 2.88 g of octyl acid and 0.54 g of water were added into a three-necked flask including a stirrer under agitation, and mineral sprits as solvent were added, then agitated vigorously to form a mixture. The mixture was heated at a temperature of 80° C. at the initial stage and was finally heated up to a temperature of 150° C. After the mixture was reacted for one hour, the mixture was heated to 120° C. under reduced pressure and the solvent was removed by vacuum distillation. The mixture was reacted at 210° C. for three hours and cooled to room temperature. Thereafter, a proper amount of n-decane was added as solvent to form 50 wt % of solution.

By the method of synthesis described above, a water-capturing or drying agent containing aluminum (Al) as a trivalent metal constituting an organometallic compound having a six-membered ring structure shown by chemical formula (13) was prepared:

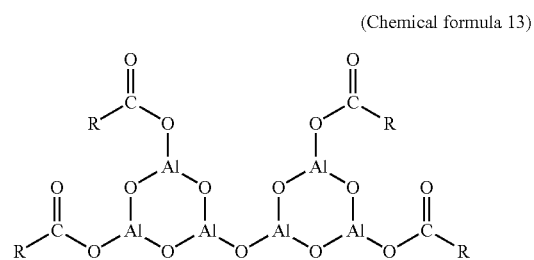

(Chemical formula 13)

By extending the reaction time, a polymer such as trimer and tetramer, shown by the chemical formulae (14), (15) and (16) was prepared:

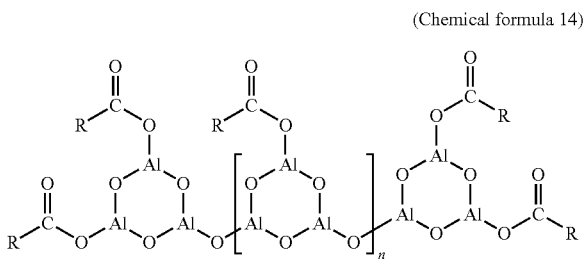

(Chemical formula 14)

wherein n is 0 or integer of 1 and above and R is $C_7H_{15}$.

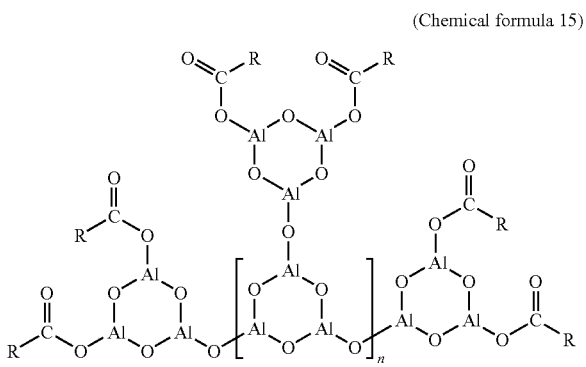

(Chemical formula 15)

wherein n is 0 or integer of 1 and above and R is $C_7H_{15}$.

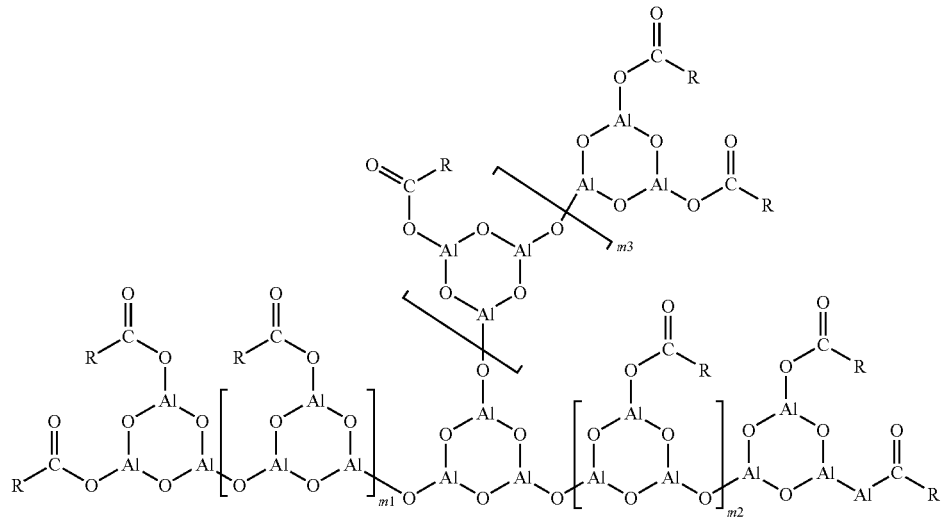

(Chemical formula 16)

wherein $m_1$, $m_2$ and $m_3$ is 0 or integer of 1 and above and R is $C_7H_{15}$.

(Preparation of an Organic EL Device and Sealing)

After an ITO-mounted glass-made substrate was cleaned, it was set in a vacuum evaporation apparatus. The vacuum evaporation apparatus was evacuated to $10^{-6}$ torr and Phthalocyanine Blue B was evaporated on the ITO-mounted glass-made substrate with a thickness of 20 nm. Then, A-NPD was evaporated onto the Phthalocyanine Blue B with a thickness of 30 nm, next a tris(8 quinolinolat)aluminum ($Alq_3$) was evaporated onto the α-NPD with a thickness of 50 nm. Thereafter, aluminum-lithium alloy was evaporated as an upper electrode onto the $Alq_3$ with a thickness of 200 nm to form a device. Next, the vacuum system was released for the vacuum evaporation apparatus and sealing was carried out in an atmosphere of dry nitrogen. An n-decane solution of the above compound was applied onto a countersunk glass-made substrate (sealing substrate) in an atmosphere of dry nitrogen. The sealing substrate onto which such solution was applied was heated to 150° C. by means of a hotplate to volatilize the solvent to solidify. After lowering the temperature of the sealing substrate to room temperature, UV-light curable epoxy adhesive was applied to the periphery of the sealing substrate to laminate the sealing substrate with a device substrate to form a laminate which was cured by irradiation with UV rays. Thereafter, the device was heated to 100° C. in an oven to adsorb moisture in the device.

(Evaluation of Water-Capturing Effect 1)

After the state of light emission of the organic EL device thus obtained was observed by a microscope, it was placed in an atmosphere of high temperature and high humidity at a temperature of 80° C. and at a humidity of 85% to confirm the water-capturing effect. Results obtained were shown in FIG. 4.

After the elapse of 100 hours, the device was taken out of such an atmosphere of high temperature and high humidity and the state of light emission of the device was observed by a microscope. As a result, no growth of a non-light emitting part, such as a darkspot, was observed and it was confirmed that the mixture of polymer of the present invention functions sufficiently as a water-capturing or drying agent. Since the water-capturing or drying agent can be formed into a uniform and transparent film, emission of EL device was confirmed through the transparent film.

A given amount of the solution of n-decane was applied onto the surface of the countersunk glass-made substrate in a gloved box, the dew point of which was −80° C. and then dried on a hotplate at 150° C. to obtain a transparent film. For comparison, calcium oxide paste was prepared comprising 50 wt % of calcium oxide (CaO) powder and 50 wt % of polymethyl methacrylate. A proper amount of the paste was applied uniformly onto the surface of the countersunk glass-made substrate by a dispenser and dried under drying conditions. Each of the two substrates coated with these drying agents was allowed to stand in air and a change in weight was observed. Results obtained were shown in FIG. 5. As a result, it was confirmed that the time required for absorbing a specific amount of moisture is short in case of the polymer synthesized by the present invention. In order to suppress the generation and growth of a darkspot or the shrinkage of a cathode, namely, lowering of function by degradation of an organic EL device, the moisture in a sealing tube should be chemically adsorbed rapidly. The water-capturing or drying agent developed by the present invention is superior to a conventional water-capturing agent with respect to water-capturing effect, and is effective to remove trace quantity of moisture in the hermetically sealed container of the organic light emission device.

Example 2

Water-Capturing or Drying Agent Formed by a Method Other Than the Dispense Coating and Mounted in an Organic EL Device The film-forming properties of the water-capturing or drying agent of the present invention are good and a uniform film can be formed on a concave or plane surface of countersunk glass by a method other than the dispense coating. The water-capturing or drying agent of the present invention was dissolved in a solvent, formed into a film on an upper surface of a sealing substrate by a spinner method, spray method, an ink jet method, a doctor blade method, a screen printing method or an offset method and heated to form a film-like water-capturing or drying agent for an organic EL device. Then, the organic EL device was made by the use of the film-like water-capturing or drying agent thus obtained. As a result, the same effect was obtained as that of Example 1.

Example 3

Water-Capturing or Drying Agent Containing the Water-Capturing or Drying Agent of Example 1 and UV-Light Curable Resin Mounted in an Organic EL Device The water-capturing or drying agent used in the organic EL device in this example has the capability of adsorbing the moisture permeating into a hermitically sealed container in which an organic EL device is sealed, or the moisture adhered to the inner surface of the hermitically sealed container or the functional part of the EL device, by using as a mixture of the water-capturing or drying agent with UV-light curable resin. The water-capturing agent and UV-light curable resin must have such a sufficient function as described below, and it is desirable that they have good compatibility with each other and can be homogeneously mixed.

(UV-Light Curing Agent)

The UV-light curing agent comprises a light transmissible monomer and a sensitizer, namely a photopolymerization initiator or photopolymerization accelerator. The light transmissible monomer can be an acrylate or methacrylate having good compatibility with the water-capturing agent of this example, such as a polyfunctional acrylate (acrylic ester), a polyfunctional methacrylate (methacrylic ester) other than mono-functional to trifunctional acrylate, or a methacrylate illustrated by chemical formulae (17) to (23). Such an acrylate or methacrylate can be used singly or in combination with each other.

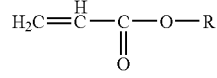

(Chemical formula 17)

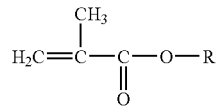

(Chemical formula 18)

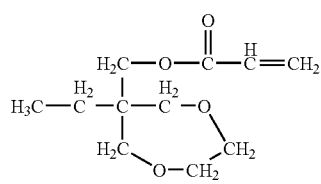

(Chemical formula 19)

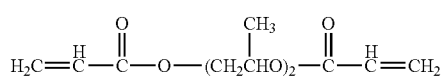

(Chemical formula 20)

(Chemical formula 21)

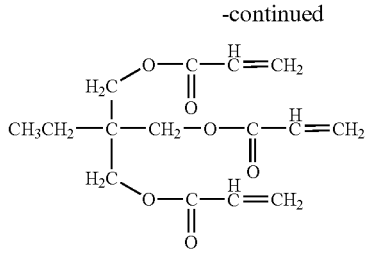

(Chemical formula 22)

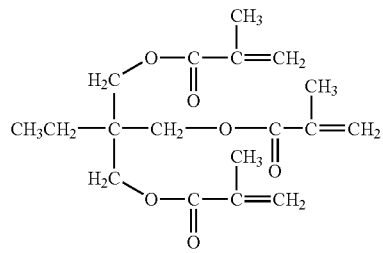

(Chemical formula 23)

Components of these UV-light curing agents are described below:

(Acrylate as Monomer)

A basic skeleton structure of an acrylic polymerizable monomer is described below.

(1) Mono-Functional Acrylate

Mono-functional acrylate is illustrated by chemical formula (17). By changing a substituent R in chemical formula (17), properties, such as the viscosity, specific gravity, index of refraction and P.I.I. value, and the like, are changed. The compatibility of such mono-functional acrylate with a water-capturing agent is changed by R. For example, in the case of the water-capturing or drying agents illustrated by chemical formulae (10) and (11), there are hydrocarbon groups comprising C and H at outer positions and a saturated aliphatic molecule dominates the compatibility of the water-capturing or drying agent. A good solvent, namely a solvent having good compatibility with the water-capturing or drying agent is, for example, a hydrocarbon solvent, such as hexane, decane, and the like, or an aromatic solvent, such as toluene, xylene, and the like. On the other hand, a solvent having low compatibility with the water-capturing or drying agent is a water-soluble solvent, such as acetone, ethanol and the like. It is, therefore, preferable that an acrylate monomer as a good solvent to the water-capturing or drying agent has two or more saturated hydrocarbon groups having two or more carbon atoms in the R, such as, methylene, and the like. Concretely, a compound illustrated by chemical formula (19) has two methylene groups or less. As the length of the saturated hydrocarbon groups in the R becomes longer, the easier the water-capturing or drying agent is dissolved.

(2) Bifunctional Acrylate

The case of a bifunctional acrylate is substantially the same as that of mono-functional acrylate. A typical example is the compound illustrated by chemical formula (20). Since the compound illustrated by chemical formula (20) contains an oxygen atom in its structure, its compatibility to the water-capturing agent is relatively slightly low compared with the compound containing a methylene group, but it can be used.

(3) Trifunctional Acrylate

The cases of a trifunctional acrylate and polyfunctional acrylate are also the same as those of the mono-functional acrylate and bifunctional acrylate. The trifunctional acrylate having methylene groups is illustrated by chemical formula (22).

(Methacrylate as Monomer)

It is considered that the case of a methacrylic photopolymerizable monomer as a component of the water-capturing or drying agent of this example is similar to that of the acrylic photopolymerizable monomer. Its basic skeleton structure is described below. Chemical formula (18) shows a general formula of the mono-functional methacrylate. Chemical formula (19) shows the mono-functional methacrylate having, as a lipophilic group, a methylene group which is a saturated hydrocarbon group containing two or more carbon atoms. Chemical formula (21) shows a bi-functional methacrylate having, as a lipophilic group, a methylene group which is a substituted saturated hydrocarbon or alkyl group. Chemical formula (23) shows tri-functional methacrylate having, as a lipophilic group, a methylene group which is a saturated hydrocarbon group containing two or more carbon atoms.

(Photosensitizer)

There are two-types of photosensitizers, one is a photoplolymerization initiator and the other is a photoplolymerization accelerator. It is preferable that the photopolymerization initiator is colorless and transparent. Even if it is colored, there is no problem, because it is added to a curing agent only in 1~3 wt % and because a cured film obtained after irradiation with UV-light becomes transparent. It is necessary to select the photopolymerization initiator which does not have an adverse effect on an organic EL device, per se. The photosensitizer is classified into two different types as described below according to reaction mechanism.

(1) Molecular Cleavage Type benzoin acrylic ether, benzyl dimethylketal, 1-hydroxycyclohexylphenylketone, 2-hydroxy-2-methyl-1-phenyl-propane-1-one, diethoxyacetophenone, 2-methyl-1-[4-(methylthio) phenyl]-2-moroholino-propane-1-one, dibenzosuberone, 2-hydroxy-2-methyl-1-phenyl-propane-1-one, diethoxyacetophenone, trichloroacetophenone.

(2) Hydrogen-Pulling Type (Photopolymerization Initiator+Photopolymerization Accelerator)

benzophenone and bisdiethylaminobenzophenone, 2,4-diethylthioxanthone and paradimethylaminobenzoic ester (2,4-diethylthioxanthone may be an aliphatic amine, for example, triethanolamine), benzyl (pulling a hydrogen atom from a hydrocarbon group which coexists with benzyl), 2-alkylanthraquinone (pulling a hydrogen atom from a hydrocarbon group which coexists with 2-alkylanthraquinone), 2-chloroanthraquinone (pulling a hydrogen atom from a hydrocarbon group which coexists with 2-chloroanthraquinone).

(Preparation of Mixture of Water-Capturing or Drying Agent Synthesized in Example 1 with the UV-Light Curing Agent)

"NK ester" (registered trademark) manufactured from SHIN NAKAMURA KAGAKU KOHGYO CO. LTD. was used as an acrylic monomer. "Irgacure 907" (registered trademark) manufactured from Ciba-Geigy was used as an initiator. Triethanolamine was used as an accelerator. These were mixed in a triethanolamine to "Irgacure 907" to "NK ester" ratio of 1:1:98 to form a UV-light curing agent. The polymer illustrated by chemical formula (1) and synthesized in Example 1 was added in such a UV-light curing agent in the same amounts by weight ratio and agitated to dissolve and form the UV-light curable water-capturing or drying agent. The UV-light curable water-capturing or drying agent thus obtained is colorless and transparent liquid.

Referring now to an organic EL device having the structure according to the embodiment shown in FIG. 2, a base substrate composed of an organic EL device was used similarly to Example 1. The base substrate was moved without exposure to air into a gloved box filled with nitrogen gas having a dew point of −60° C. A sealing substrate made of 0.70 mm thick glass having a 0.2 mm deep recess formed by a countersinking process was cleaned in advance and dehydrated by heating to 150° C. and put into the gloved box. Then, a mixture of the water-capturing or drying agent synthesized in Example 1 with the UV-light curing agent was applied to the inner surface of the recess with a thickness of about 8 $\mu/cm^2$ by the use of a dispenser and irradiated with UV-light having wavelength of 365 nm at 100 nW/cm$^2$ for 60 sec. Then, the mixture was cured and adhered onto the inner surface of the recess. The sealing part in the recess of the sealing substrate was coated with UV-light sealing agent containing beads of 10 μm diameter, and was laminated onto the device substrate and irradiated from the side of the sealing substrate with UV-light having main wavelength of 365 nm at 100 nW/cm$^2$ for 60 seconds to complete sealing.

The device thus formed was allowed to stand in an atmosphere of high temperature of 85° C. and high humidity of 85% to carry out accelerated life-test. After the elapse of 100 hours, the state of light emission of the device was substantially the same as prior to such test. The generation and growth of a non-light emitting part, such as a darkspot, were suppressed and it was confirmed that the water-capturing or drying agent of the present invention functions sufficiently.

Since the above water-capturing or drying agent can be formed into a uniform and transparent film, emission of EL device was confirmed through the transparent film.

Example 4

Example 4 is relating to an example in which the water-capturing or drying agent of Example 3 was formed into a film by a method other than a dispense coating and mounted in an organic EL device. The water-capturing or drying agent of the present invention has an excellent film-forming performance and can form a uniform film on a countersunk glass or flat plate. In the example, the water-capturing or drying agent of the present invention was dissolved in a solvent, formed into a film on an upper surface of a sealing substrate by one of a spinner method, spray method, an ink jet method, a doctor blade method, a screen printing method or an offset method and heated to form a film-shaped water-capturing, and drying agent for an organic EL device. Then, an organic El device was made by the use of the film-shaped water-capturing or drying agent thus obtained. As a result, the same effect was obtained as that of Example 1.

Example 5

Example 5 is relating to an example in which the water-capturing or drying agent of the present invention was used in an inorganic water barrier layer formed on the surface of an organic EL device having the structure shown in FIG. 3. In Example 5, a base substrate composed of an organic EL device was used similarly to Example 1. The base substrate was moved without exposure to air into a gloved box containing nitrogen gas and having a dew point of −60° C. In such a gloved box, a mixture of the water-capturing or drying agent synthesized in Example 1 with the curing agent (the same water-capturing or drying agent as that of Example 4) was applied onto a cathode in a stripped patter with 5 mm intervals by the use of a dispenser. A sealing substrate made of glass cleaned in advance and dehydrated by heating to 150° C. was put into the gloved box and mounted onto the base substrate.

Then, a mixture of the water-capturing or drying agent synthesized in Example 1 with the UV-light curing agent was applied over the entire surface of the cathode by applying pressure between the base substrate and the sealing substrate. Thereafter, UV-light sealing agent was applied between the outer periphery of the sealing substrate and the base substrate and irradiated with UV-light having main wavelength of 365 nm at 100 nW/cm² for 60 sec. from the sealing device to complete sealing.

The device thus formed was allowed to stand in an atmosphere of high temperature of 85° C. and high humidity of 85% to carry out accelerated life test. After the elapse of 100 hours, the state of light emission of the device was substantially the same as that prior to such a test. The generation and growth of a non-light emitting part, such as a darkspot, were suppressed and it was confirmed that water-capturing or drying agent of the present invention functions sufficiently.

Since the water-capturing or drying agent of Example 5 can form a uniform and transparent film-shaped drying member, the light emission of the EL device was confirmed through the transparent film-shaped drying member.

Examples of water-capturing or drying agent containing metal other than Al as trivalent metal constituting an organometallic compound having a multi-membered ring structure will be described below.

Example 6

A Water-Capturing or Drying Agent Containing Gallium (Ga) as a Trivalent Metal Constituting an Organometallic Compound Having a Six-Membered Ring Structure (Method of synthesis) 7.40 g of gallium-triisopropoxide (GIP), 2.88 g of octylic acid and 0.54 g of water were added with stirring into a three-necked flask into which was put a stirrer. Then, mineral spirits were added and the solution was vigorously agitated and heated to a temperature of 80° C. at first. The temperature of the solution was gradually increased and finally heated to 150° C. After reaction for one hour, the solution was heated to 210° C. while reducing pressure to distil the solvent under reduced pressure. After reaction at 210° C. for three hours, the solution was cooled to a room temperature. Thereafter, a suitable amount of n-decane was added as a solvent to prepare a 50% solution.

By the above method of synthesis, a drying agent containing gallium (Ga) instead of aluminum (Al) as a trivalent metal constituting an organometallic compound having a six-membered ring structure shown by chemical formula 13 was prepared.

(Chemical formula 24)

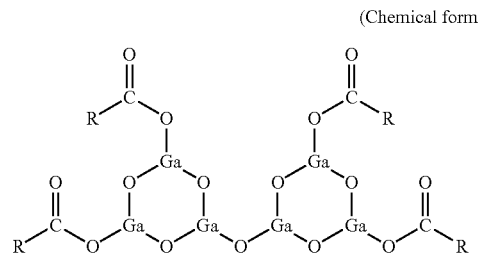

wherein R is $C_7H_{15}$.

By extending the reaction time, a polymer such as trimer, tetramer, and so forth containing gallium (Ga) instead of aluminum (Al) as a trivalent metal (M) was synthesized, similarly to compounds shown by chemical formulae (14), (15) and (16).

(Preparation of an Organic EL Device and Sealing)

An organic EL device was prepared by the use of the water-capturing or drying agent of Example 6 for that of Example 1 similar to Examples 2~5 and evaluated. The state of emission of the organic EL device was observed by the use of a microscope and put in an atmosphere of high temperature of 85° C. and high humidity of 85% to confirm water-capturing effect. After an elapse of 100 hours, the device was taken out of such an atmosphere and the state of emission of the organic EL device was observed by the use of a microscope. As a result, a non-light emitting part was not observed and it was confirmed that the drying agent functions sufficiently as a water-capturing or drying agent.

Since the water-capturing agent of Example 6 can form a uniform and transparent film-shaped drying member, the light emission of the EL device was confirmed through the transparent film-shaped drying member.

Example 7

A Water-Capturing or Drying Agent Containing Indium (In) as a Trivalent Metal Constituting an Organometallic Compound Having a Multi-Membered Ring Structure 8.75 g of indium-triisopropoxide, 2.88 g of octylic acid and 0.54 g of water were added with stirring into a three-necked flask into which was put a stirrer. Then, mineral spirits were added and the solution was vigorously agitated and heated to a temperature of 80° C. at first. The temperature of the solution was gradually increased and finally heated to 150° C. After reaction for one hour, the solution was heated to 210° C. while reducing pressure to distil the solvent under reduced pressure. After reaction at 210° C. for three hours, the solution was cooled to a room temperature. Then, a suitable amount of n-decane was added as solvent to prepare a 50% solution.

By the above method of synthesis, a drying agent containing indium (In) instead of aluminum (Al) as a trivalent metal (M) constituting an organometallic compound having a six-membered ring structure shown by chemical formula (13) was prepared.

(Chemical formula 25)

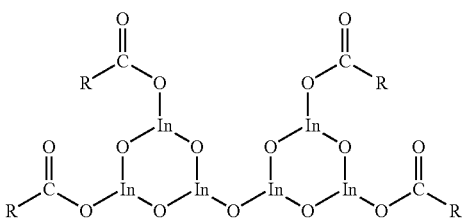

wherein R is $C_7H_{15}$.

By extending the reaction time, a polymer such as trimer, tetramer, and so forth containing indium (In) instead of aluminum (Al) as a trivalent metal (M) was synthesized, similar to compounds shown by chemical formula 14, chemical formula 15 and chemical formula 16.

(Preparation of an Organic EL Device and Sealing)

An organic EL device was prepared by the use of the water-capturing or drying agent of Example 6 for that of Example 1, similar to Examples 1~5 and evaluated. The state of emission of the organic EL device was observed by the use of a microscope and put in an atmosphere of high temperature of 85° C. and high humidity of 85% to confirm water-capturing effect. After an elapse of 100 hours, the device was taken out of such an atmosphere and the state of emission of the organic EL device was observed by the use of a microscope. As a result, a non-light emitting part was not observed and it was confirmed that the drying agent functions sufficiently as a water-capturing or drying agent.

Since the water-capturing agent of Example 7 can form a uniform and transparent film-shaped drying member, the light emission of the EL device was confirmed through the transparent film-shaped drying member.

Example 8

A Water-Capturing or Drying Agent Containing Yttrium (Y) as a Trivalent Metal (M) Constituting an Organometallic Compound Having a Multi-Membered Ring Structure (Method of Synthesis)

7.99 g of yttrium-triisopropoxide, 2.88 g of octylic acid and 0.54 g of water were added with stirring into a three-necked flask into which was put a stirrer. Then, mineral spirits were added and the solution was vigorously agitated and heated to a temperature of 80° C. at first. The temperature of the solution was gradually increased and finally heated to 150° C. After reaction for one hour, the solution was heated to 210° C. while reducing pressure to distil the solvent under reduced pressure. After reaction at 210° C. for three hours, the solution was cooled to a room temperature. Then, a suitable amount of n-decane was added as solvent to prepare a 50% solution.

By the above method of synthesis, a drying agent containing yttrium (Y) instead of aluminum (Al) as a trivalent metal (M) constituting an organometallic compound having a six-membered ring structure shown by chemical formula (13) was prepared.

(Chemical formula 26)

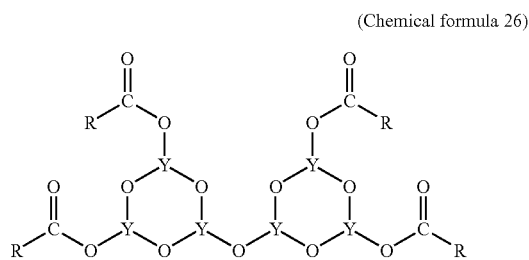

wherein R is $C_7H_{15}$.

By extending the reaction time, a polymer such as trimer, tetramer, and so forth containing yttrium (Y) instead of aluminum (Al) as a trivalent metal (M) was synthesized, similar to compounds shown by chemical formulae (14), (15) and (16).

(Preparation of an Organic EL Device and Sealing)

An organic EL device was prepared by the use of the water-capturing or drying agent of Example 6 for that of Example 1, similar to Examples 1~5 and evaluated. The state of emission of the organic EL device was observed by the use of a microscope and put in an atmosphere of high temperature of 85° C. and high humidity of 85% to confirm water-capturing effect. After an elapse of 100 hours, the device was taken out of such an atmosphere and the state of emission of the organic EL device was observed by the use of a microscope. As a result, a non-light emitting part was not observed and it was confirmed that the drying agent functions sufficiently as a water-capturing agent.

Since the water-capturing or drying agent of Example 8 can form a uniform and transparent film-shaped drying member, the light emission of the EL device was confirmed through the transparent film-shaped drying member.

Example 9

A Water-Capturing or Drying Agent Containing Lanthanum (La) as a Trivalent Metal (M) Constituting an Organometallic Compound Having a Multi-Membered Ring Structure (Method of Synthesis)

9.48 g of lanthanum-triisopropoxide, 2.88 g of octylic acid and 0.54 g of water were added with stirring into a three-necked flask into which was put a stirrer. Then, mineral spirits were added and the solution was vigorously agitated and heated to a temperature of 80° C. at first. The temperature of the solution was gradually increased and finally heated to 150° C. After reaction for one hour, the solution was heated to 210° C. while reducing pressure to distil the solvent under reduced pressure. After reaction at 210° C. for three hours, the solution was cooled to a room temperature. Thereafter, a suitable amount of n-decane was added as solvent to prepare a 50% solution.

By the above method of synthesis, a drying agent containing lanthanum (La) instead of aluminum (Al) as trivalent metal (M) constituting an organometallic compound having a six-membered ring structure shown by chemical formula (13) was prepared.

(Chemical formula 27)

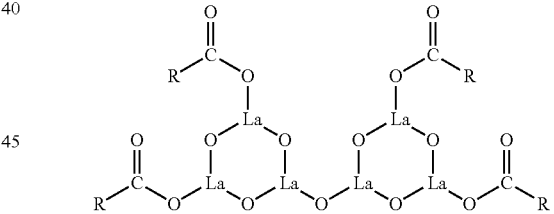

wherein R is $C_7H_{15}$.

By extending the reaction time, a polymer such as trimer, tetramer and so forth containing lanthanum (La) instead of aluminum (Al) as a trivalent metal (M) was synthesized, similar to compounds shown by chemical formulae (14), (15) and (16).

(Preparation of an Organic EL Device and Sealing)

An organic EL device was prepared by the use of the water-capturing or drying agent of Example 6 for that of Example 1, similarly to Examples 1~5 and evaluated. The state of emission of the organic EL device was observed by the use of a microscope and put in an atmosphere of high temperature of 85° C. and high humidity of 85% to confirm water-capturing effect. After an elapse of 100 hours, the device was taken out of such an atmosphere and the state of emission of the organic EL device was observed by the use of a microscope. As a result, a non-light emitting part was not observed and it was confirmed that the drying agent functions sufficiently as a water-capturing agent.

Since the water-capturing or drying agent of Example 9 can form a uniform and transparent film-shaped drying member, the light emission of the EL device was confirmed through the transparent film-shaped drying member.

As described above, it was recognized that the water-capturing or drying agent containing Al, Ga, In, Y or La as trivalent metal (M) constituting an organometallic compound having a multi-membered ring structure multi-membered ring structure has a water-capturing effect for an organic EL device. It is, therefore, understood that trivalent metal (M) constituting an organometallic compound having a multi-membered ring structure functions as a water-capturing or drying agent.

The drying agent of the present invention is useful for a water-capturing or drying agent for an electronic part used in a sealed container. According to the present invention, the water-capturing or drying agent is placed in a sealed container of an organic or inorganic EL device which is composed of mainly a fluorescent organic or inorganic compound. The water-capturing or drying agent of the present invention is capable of providing a low-profile El device which is hardly susceptible to water or oxygen over the long term and which is able to maintain stable emission. Furthermore, the drying agent of the present invention is a transparent film and absorbs water rapidly. Thus, it can be used as a water-capturing or drying agent for an electronic part sealed in a hermetic sealed container.

Obviously, many modifications and variations of the present invention are possible in the light of the above teachings. It is therefore to be understood that within the scope of the appended claims, the invention may be practiced otherwise than as specifically described.

What is claimed is:

1. A field light emission device comprising a light emission layer and a drying agent placed in a hermetically sealed container, wherein the drying agent is selected from compounds as illustrated by chemical formula (2);

(Chemical formula 2)

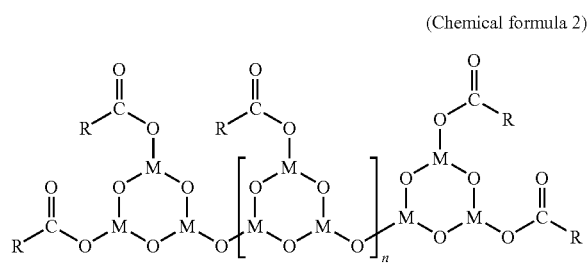

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer, and n is 0 or an integer of 1 and above; and Wherein M is a trivalent metal atom.

2. A field light emission device comprising a light emission layer and a drying agent containing a ultraviolet light-curing agent placed in a hermetically sealed container, wherein the drying agent is selected from at least one compound as illustrated by chemical formula (2);

(Chemical formula 2)

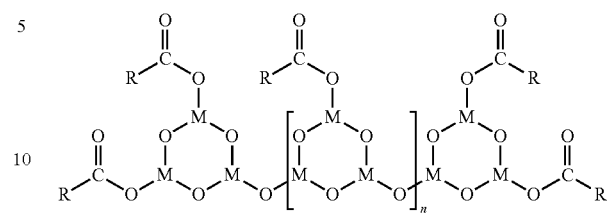

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer, and n is 0 or an integer of 1 and above; and Wherein M is a trivalent metal atom.

3. A field light emission device as defined in claim 2, wherein the ultraviolet light-curing agent is a light transmissible monomer having a lipophilic group.

4. A field light emission device comprising a light emission layer and a drying agent placed in a hermetically sealed container, wherein the drying agent is selected from a compound illustrated by chemical formula (3);

(Chemical formula 3)

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer, and n is 0 or an integer of 1 and above; and Wherein M is a trivalent metal atom.

5. A field light emission device comprising a light emission layer and a drying agent containing a ultraviolet light-curing agent placed in a hermetically sealed container, wherein the drying agent is selected from at least one compound as illustrated by chemical formula (3);

(Chemical formula 3)

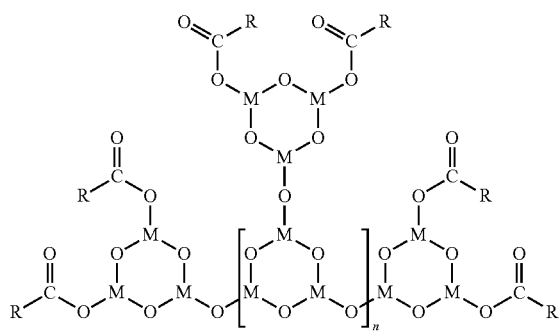

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer, and n is 0 or an integer of 1 and above; and Wherein M is a trivalent metal atom.

6. A field light emission device as defined in claim 5, wherein the ultraviolet light-curing agent is a light transmissible monomer having a lipophilic group.

7. A field light emission device comprising a light emission layer and a drying agent placed in a hermetically sealed container, wherein the drying agent is selected from compounds as illustrated by chemical formula (4);

(Chemical formula 4)

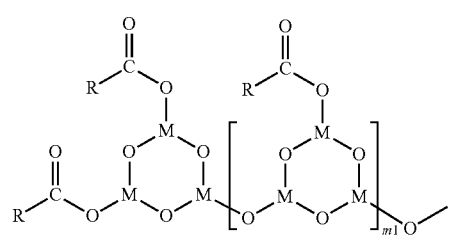

-continued

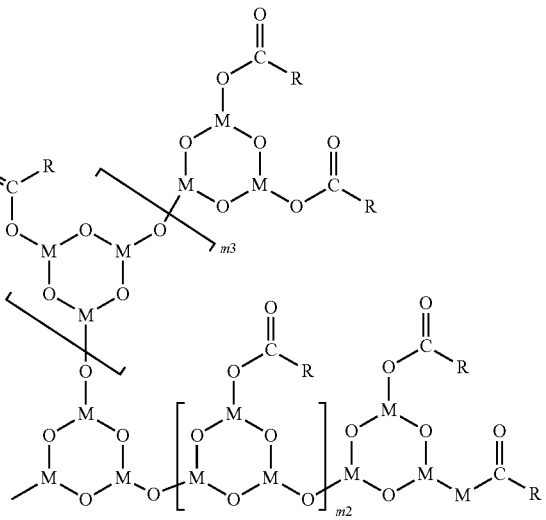

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer;

Wherein $m_1$, $m_2$ and $m_3$ are an integer of 1 and above and may be different each other or same each other; and Wherein M is a trivalent metal atom.

8. A field light emission device comprising a light emission layer and a drying agent containing a ultraviolet light-curing agent placed in a hermetically sealed container, wherein the drying agent is selected from at least one compound as illustrated by chemical formula (4);

(Chemical formula 4)

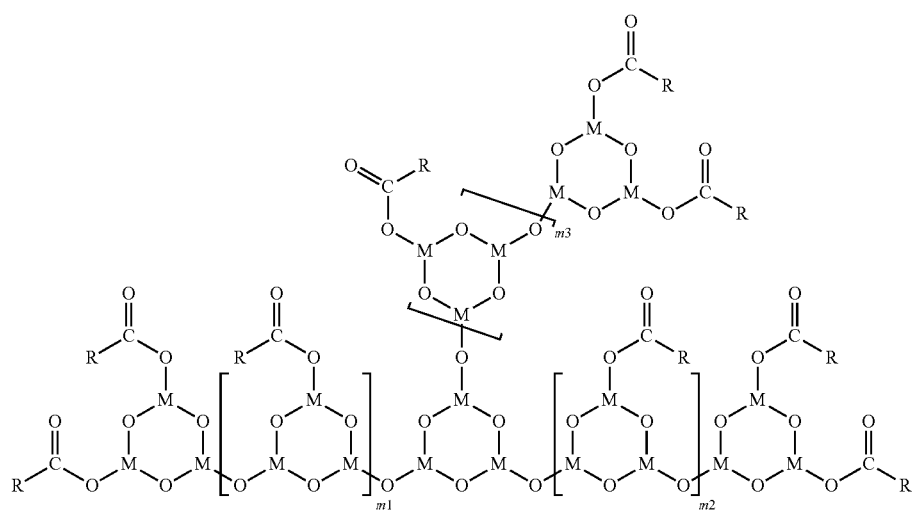

Wherein, R is a hydrogen atom or an alkyl group, aryl group, cycloalkyl group, heterocyclic ring group having one or more carbon atoms;

Wherein one or more hydrogen atoms in each of groups may be substituted for a halogen atom;

Wherein R may be from different groups, may be from the same group, may be bonded to each other, or may be a polymer;

Wherein $m_1$, $m_2$ and $m_3$ are an integer of 1 and above and may be different each other or same each other; and Wherein M is a trivalent metal atom.

9. A field light emission device as defined in claim 8, wherein the ultraviolet light-curing agent is a light transmissible monomer having a lipophilic group.

* * * * *

UNITED STATES PATENT AND TRADEMARK OFFICE
CERTIFICATE OF CORRECTION

| | | |
|---|---|---|
| PATENT NO. | : 7,871,712 B2 | Page 1 of 1 |
| APPLICATION NO. | : 11/386367 | |
| DATED | : January 18, 2011 | |
| INVENTOR(S) | : Takahashi et al. | |

It is certified that error appears in the above-identified patent and that said Letters Patent is hereby corrected as shown below:

Column 4, line 30 "caturing" should be -- capturing --

Signed and Sealed this
Twelfth Day of April, 2011

David J. Kappos
*Director of the United States Patent and Trademark Office*